US009655526B2

(12) United States Patent
Hu

(10) Patent No.: US 9,655,526 B2
(45) Date of Patent: May 23, 2017

(54) VITAL SIGNS FIBER OPTIC SENSOR SYSTEMS AND METHODS

(71) Applicant: Darma Inc., Palo Alto, CA (US)

(72) Inventor: Junhao Hu, Singapore (SG)

(73) Assignee: SHENZHEN DARMA TECHNOLOGY CO., LTD., Shenzhen, Guangdong Province (CN)

( * ) Notice: Subject to any disclaimer, the term of this patent is extended or adjusted under 35 U.S.C. 154(b) by 0 days.

(21) Appl. No.: 14/872,040

(22) Filed: Sep. 30, 2015

(65) Prior Publication Data

US 2016/0089031 A1    Mar. 31, 2016

Related U.S. Application Data

(60) Provisional application No. 62/057,237, filed on Sep. 30, 2014.

(51) Int. Cl.
*A61B 5/00* (2006.01)
*A61B 5/0476* (2006.01)
(Continued)

(52) U.S. Cl.
CPC ............ *A61B 5/0082* (2013.01); *A61B 5/021* (2013.01); *A61B 5/0205* (2013.01);
(Continued)

(58) Field of Classification Search
CPC ... A61B 5/0082; A61B 5/1102; A61B 5/0476; A61B 5/7257; A61B 5/021;
(Continued)

(56) References Cited

U.S. PATENT DOCUMENTS 4,618,764 A * 10/1986 Harmer .................. G01B 11/18
250/227.14
4,770,492 A *  9/1988 Levin ................. G02B 6/03611
250/227.14
(Continued)

FOREIGN PATENT DOCUMENTS

CN       103575313 A    2/2014
EP         1099965 A2    5/2001
(Continued)

OTHER PUBLICATIONS

Wikipedia article for "Bend radius" as archived on Jun. 27, 2013.*
(Continued)

*Primary Examiner* — Long V Le
*Assistant Examiner* — Colin T Sakamoto
(74) *Attorney, Agent, or Firm* — Cheng-Ju Chiang

(57) ABSTRACT

An intensity-based, micro-bending optical fiber sensor is disclosed herein, which is configured to acquire clean, stable, and reliable vital sign signals. Related systems and methods for vital sign monitoring are also provided herein. The sensor of various embodiments includes a multi-mode optical fiber, an LED light source, an LED driver, a receiver, and a single layer deformer structure. In various embodiments, the optical fiber and single layer deformer structure of the sensor are selected to meet specific parameters necessary to achieve a level of reliability and sensitivity needed to successfully monitor vital signs. In some embodiments, a specific sizing relationship exists between the optical fiber and the single layer deformer structure. In sonic embodiments, the sensor is configured to acquire ballistocardiograph waveforms.

2 Claims, 8 Drawing Sheets

(51) Int. Cl.
*A61B 5/021* (2006.01)
*A61B 5/11* (2006.01)
*A61B 5/0205* (2006.01)
*G01L 1/24* (2006.01)
*A61B 5/024* (2006.01)
*A61B 5/08* (2006.01)

(52) U.S. Cl.
CPC .......... *A61B 5/0476* (2013.01); *A61B 5/1102* (2013.01); *A61B 5/1116* (2013.01); *A61B 5/4812* (2013.01); *A61B 5/6892* (2013.01); *A61B 5/7207* (2013.01); *A61B 5/7257* (2013.01); *A61B 5/0022* (2013.01); *A61B 5/02405* (2013.01); *A61B 5/0816* (2013.01); *A61B 5/1123* (2013.01); *A61B 5/6891* (2013.01); *A61B 5/746* (2013.01); *A61B 2562/0233* (2013.01); *G01L 1/245* (2013.01)

(58) Field of Classification Search
CPC ... A61B 5/6892; A61B 5/4812; A61B 5/0205; A61B 5/1116; A61B 5/7207; A61B 2562/0233; A61B 5/0022; A61B 5/6891; G01L 1/245
See application file for complete search history.

(56) References Cited

U.S. PATENT DOCUMENTS

| | | | |
|---|---|---|---|
| 4,822,135 A | 4/1989 | Seaver | |
| 4,863,270 A | 9/1989 | Spillman | |
| 5,067,815 A * | 11/1991 | Kotrotsios | G01L 1/245 250/227.16 |
| 5,132,529 A * | 7/1992 | Weiss | G01L 1/245 250/227.16 |
| 5,134,281 A | 7/1992 | Bryenton et al. | |
| 5,193,129 A * | 3/1993 | Kramer | G01L 1/245 250/227.14 |
| 5,212,379 A | 5/1993 | Nafarrate et al. | |
| 5,241,300 A | 8/1993 | Buschmann | |
| 5,291,013 A | 3/1994 | Nafarrate et al. | |
| 5,321,257 A | 6/1994 | Danisch | |
| 5,348,019 A * | 9/1994 | Sluss, Jr. | A61B 5/037 600/480 |
| 5,357,813 A * | 10/1994 | Weinberger | G08B 13/10 73/800 |
| 5,678,266 A | 10/1997 | Petringa et al. | |
| 5,818,982 A | 10/1998 | Voss et al. | |
| 5,926,584 A * | 7/1999 | Motzko | G01L 1/245 250/227.14 |
| 5,942,750 A * | 8/1999 | Sannerhaugen | G01B 11/18 250/227.14 |
| 5,953,468 A | 9/1999 | Finnila et al. | |
| 6,079,875 A | 6/2000 | Klass et al. | |
| 6,381,482 B1 | 4/2002 | Jayaraman et al. | |
| 6,498,652 B1 | 12/2002 | Varshneya et al. | |
| 6,687,523 B1 | 2/2004 | Jayaramen et al. | |
| 6,711,330 B1 | 3/2004 | Donlagic | |
| 6,816,266 B2 | 11/2004 | Varshneya et al. | |
| 7,046,900 B2 | 5/2006 | Kondo et al. | |
| 7,196,317 B1 | 3/2007 | Meissner, II et al. | |
| 7,532,781 B2 | 5/2009 | Thompson et al. | |
| 7,605,923 B2 | 10/2009 | Williams et al. | |
| 7,957,623 B2 | 6/2011 | Panarello et al. | |
| 8,111,953 B2 | 2/2012 | Borgos et al. | |
| 8,206,324 B2 | 6/2012 | Kurono et al. | |
| 8,277,384 B2 | 10/2012 | Fine | |
| 8,376,954 B2 | 2/2013 | Lange et al. | |
| 8,403,865 B2 | 3/2013 | Halperin et al. | |
| 8,491,492 B2 | 7/2013 | Shinar et al. | |
| 8,502,679 B2 | 8/2013 | Ayon et al. | |
| 8,679,030 B2 | 3/2014 | Shinar et al. | |
| 8,679,034 B2 | 3/2014 | Halperin et al. | |
| 8,731,646 B2 | 5/2014 | Halperin et al. | |
| 8,750,971 B2 | 6/2014 | Tran | |
| 8,882,684 B2 | 11/2014 | Halperin et al. | |
| 2002/0076149 A1 | 6/2002 | Deacon | |
| 2002/0193707 A1 | 12/2002 | Atlas et al. | |
| 2003/0038231 A1 | 2/2003 | Bryant et al. | |
| 2005/0124864 A1* | 6/2005 | Mack | A61B 5/024 600/300 |
| 2010/0259831 A1 | 10/2010 | Patterson | |
| 2011/0043898 A1 | 2/2011 | Grunsteidl et al. | |
| 2011/0275939 A1 | 11/2011 | Walsh et al. | |
| 2012/0203117 A1* | 8/2012 | Chen | A61B 5/1102 600/484 |
| 2013/0188971 A1 | 7/2013 | Painchaud | |
| 2014/0077722 A1 | 3/2014 | Takacs et al. | |
| 2015/0018637 A1* | 1/2015 | Chen | A61B 5/0059 600/301 |

FOREIGN PATENT DOCUMENTS

| | | |
|---|---|---|
| GB | 2197953 A | 6/1988 |
| JP | 2005043087 A | 2/2005 |
| WO | 9410877 A1 | 5/1994 |
| WO | 0215748 A1 | 2/2002 |
| WO | 2005074754 A1 | 8/2005 |
| WO | 2009104127 A1 | 8/2009 |
| WO | 2013179189 A1 | 12/2013 |
| WO | 2014085302 A1 | 6/2014 |
| WO | 2014151577 A1 | 9/2014 |

OTHER PUBLICATIONS

T. Allsop, G. Lloyd, R. S. Bhamber, L. Hadzievski, M. Halliday, D. J. Webb, and I. Bennion, "Cardiac-induced localized thoracic motion detected by a fiber optic sensing scheme," J. Biomed. Opt, vol. 19, No. 11, pp. 117006-1-117006-10, Nov. 2014.

R. Casanella, J. Gomez-Clapers, "On time interval measurements using BCG," 34th Ann. Int Conf of the IEEE Eng in Med. and Bio Soc, 2012, Aug. 28-Sep. 1, 2012, pp. 5034-5037.

Z. Chen, D. Lau, J. T. Teo, S. H. Ng, X. Yang, and P. L. Kei, "Field test of microbend fiber sensor for hospital use," 23rd International Conference on Optical Fibre Sensors, Proc. of SPIE, vol. 9157, 2014, pp. 91579A-1-91579A-4.

Z. Chen, D. Lau, J. T. Teo, S. H. Ng, X. Yang, and P. L. Kei, "Simultaneous measurement of breathing rate and heart rate using a microbend multimode fiber optic sensor," J. Biomed. Opt, vol. 19, No. 5, pp. 057001-1-057001-11, May 2014.

Z. Chen, J. T. Teo, S. H. Ng, and X. Yang, "Portable fiber optic ballistocardiogram sensor for home use," Proc. of SPIE, vol. 8218, 2012, pp. 82180X-1-82180X-7.

C. J. Deepu, Z. Chen, J. T. Teo, S. H. Ng, X. Yang, and Y. Lian, "A smart cushion for real-time heart rate monitoring," in 2012 IEEE Biomed Cir and Sys Conf, 2012, pp. 53-56.

Ł. Dziuda, "Fiber-optic sensors for monitoring patient physiological parameters," J. Biomed. Opt, vol. 20, No. 1, pp. 010901-1-010901-23, 2015.

J. Gomez-Clapers, "Towards the standardization of ballistocardiography systems for J-peak timing measurement," Measurement, vol. 58, pp. 310-316, Dec. 2014.

R. González-Landaeta, O. Casas, and R. Pallàs-Areny, "Heart rate detection from an electronic weighing scale," Physiol Meas, vol. 29, No. 8, pp. 979-988, Aug. 2008.

A. Grillet, D. Kinet, J. Witt, M. Schukar, "Optical Fiber Sensors Embedded Into Medical Textiles for Healthcare Monitoring," IEEE Sens J., vol. 8, No. 7, pp. 1215-1222, Jul. 2008.

M. Krehel, M. Schmid, R. M. Rossi, L. F. Boesel, G.-L. "An Optical Fibre-Based Sensor for Respiratory Monitoring," Sensors, vol. 14, No. 7, pp. 13088-13101, Jul. 2014.

N. Lagakos, J. H. Cole, and J. A. Bucaro, "Microbend fiber-optic sensor," Appl. Opt., vol. 26, No. 11, pp. 2171-2180, Jun. 1987.

Joan Gomez-Clapers, Albert Serra, Ramon Casanella, Rocamora, Albert Serra, Clapers, Joan Gomez, and IMEKO, "Uncertainty factors in time-interval measurements in ballistocardiography," 19th

(56) References Cited

OTHER PUBLICATIONS

Symposium IMEKO TC 4 Symposium and 17th IWADC Workshop Advances in Instrumentation and Sensors Interoperability, Jul. 18-19, 2013, pp. 395-399.
M. Rothmaier, M. P. Luong, and F. Clemens, "Textile Pressure Sensor Made of Flexible Plastic Optical Fibers," Sensors, vol. 8, No. 7, pp. 4318-4329, Jul. 2008.
M. Rothmaier, B. Selm, S.Spichtig, D. Haensse, and M. Wolf, "Photonic textiles for pulse oximetry," Opt. Express, vol. 16, No. 17, pp. 12973-12986, Aug. 2008.
W. B. Spillman Jr, M. Mayer, J. Bennett, J. Gong, K. E. Meissner, B. Davis, R. O. Claus, A. A. MuelenaerJr, and X. Xu, "A smart bed for non-intrusive monitoring of patient physiological factors," Measurement Sciand Tech, v. 15, No. 8, pp. 1614-1620, Aug. 2004.
S. Šprager, D. Donlagic, and D. Zazula, "Monitoring of basic human vital functions using optical interferometer," in 2010 IEEE 10th Int Conf on Signal Proc.(ICSP), 2010, pp. 1738-1741.
E. Udd, "An overview of fiber-optic sensors," Review of Scientific Instruments, vol. 66, No. 8, pp. 4015-4030, Aug. 1995.
W. S. Fegadolli, "Plastic Optical Fiber Microbend Sensors," PIERS Proceedings, Jul. 2-6, 2008, pp. 842-845.
Y. Zhu, H. Zhang, M. Jayachandran, A. K. Ng, J. Biswas, and Z. Chen, "Ballistocardiography with fiber optic sensor in headrest position: A feasibility study and a new processing algorithm," 35th Annual International Conference of the IEEE Eng Med Biol Soc, Jul. 3-7, 2013, p. 5203-5206, 2013.
Axia Smart Chair—your personal posture coach—BMA Ergonomics, viewed Jul. 16, 2015 at http://www.bma-ergonomics.com/en/product/axia-smart-chair/#ad-image-0, 5 pages.
V. De Lalla et al., "Analysis of H Wave of Ballistocardiogram," Circulation, vol. 11, Nov. 1950, pp. 765-769.
L. Giovangrandi et al., "Ballistocardiography—A Method Worth Revisiting," Conf Proc IEEE Eng Med Biol Soc., Author manuscript; available in PMC Dec. 23, 2014, pp. 1-10.
S. Haveman et al., "Smart monitoring of worker posture in an office environment," viewed on Jul. 31, 2015 at http://wwwhome.cs.utwente.nl/~kant/docs/Worker%20Posture%20Monitoring.pdf, pp. 1-17.
G. Keiser et al., "Review of diverse optical fibers used in biomedical research and clinical practice," Journal of Biomedical Optics vol. 19(8), Aug. 2014, pp. 080902-1-080902-29.
D. Lau et al., "Intensity-Modulated Micro-bend Fiber Optic Sensor for Respiratory Monitoring and Gating During MRI," viewed online Jul. 31, 2015 at http://oar.a-star.edu.sg/jspui/bitstream/123456789/181/3/IEEE_Manuscript_Final%20Revisionzhihao.pdf, pp. 1-10.
H. Lee, et al., "Ultra-low-loss optical delay line on a silicon chip," Nature Communications 3, Article No. 867, May 29, 2012, 11 pages.
C. Mattmann et al., "Recognizing Upper Body Postures Using Textile Strain Sensors," IEEE, 1-4244-1453-9/07, Sep. 2007, 8 pages.
M. Nishyama et al., "Respiration and body movement analysis during sleep iin bed using hetero-corre fiber optic pressure sensors without constraint to human activity," Journal of Biomedical Optics, vol. 16(1), Jan. 2011, pp. 017002-1-017002-7.
E. Pinheiro et al., "Study on Ballistocardiogram Acquisition in a Moving Wheelchair with Embedded Sensors," Metrology and Measurement Systems, vol. XIX (2012), No. 4, Dec. 15, 2012, pp. 739-750.
E. Pinheiro et al., "Theory and Developments in an Unobtrusive Cardiovascular System Representation: Ballistocardiography," The Open Biomedical Engineering journal, vol. 4, 2010, pp. 201-216.
O. Postolache et al., "Seismocardiogram and Ballistocardiogram Sensing," International Journal of Measurement Technologies and Instrumentation Engineering, 1(3), pp. 67-88, Jul.-Sep. 2011.
Prevent Poor Posture with the Smart Ergonomic Chair, accessed online at: https://www.utmb.edu/tstem/tstemutil/Uploads/2035_PreventPoorPosture.pdf, 10 pages.
S. Sprager, et al., "Heartbeat and Respiration Detection from Optical Interferometric Signals by Using a Multimethod Approach," IEEE Transactions on Biomedical Engineering, vol. 59, No. 10, Oct. 2012, pp. 2922-2929.
E. Suaste-Gomez et al., "Electrically Insulated Sensing of Respiratory Rate and Heartbeart Using Optical Fibers," Sensors 2014, 14, Nov. 14, 2014, pp. 21523-21534.
J. Witt et al., "Medical TextilesWith Embedded Fiber Optic Sensors for Monitoring of Respiratory Movement," IEEE Sensors Journal, vol. 12, No. 1, Jan. 2012, pp. 246-254.
D. Zazula et al., "Application of Fibre-Optic Interferometry to Detection of Human Vital Signs," Journal of the Laser and Health Academy vol. 2012, No. 1, Summaries of LAHA and KC BME Symposium 2012, pp. S27-S32.
International Search Report and Written Opinion mailed Sep. 18, 2015 from International Application No. PCT/US2015/035721, 15 pages.
International Search Report and Written Opinion mailed Dec. 29, 2015 from International Application No. PCT/US2015/053369, 9 pages.

\* cited by examiner

VITAL SIGNS FIBER OPTIC SENSOR SYSTEMS AND METHODS

CROSS-REFERENCE TO RELATED APPLICATIONS

This application claims the benefit under 35 U.S.C. §119 (e) of Provisional Application 62/057,237 filed Sep. 30, 2014, which is herein incorporated by reference in its entirety.

TECHNICAL FIELD

This application generally relates to the field of fiber optics, and particularly, to optical fiber sensors and methods for monitoring physiological parameters of a patient.

BACKGROUND

With the advent of internet-connected devices and the digital health industry, health and wellness monitoring has become an area of growing focus. Monitoring vital signs such as heart rate, ballistocardiogram signals, and breathing rate is desirable both inside and outside healthcare facilities. Within healthcare settings, vital sign tracking can be essential for: ensuring patient safety when a healthcare provider is not present at a bedside, diagnosing medical conditions, monitoring a patient's progress, and planning a patient's care. Outside of healthcare settings, tracking vital signs and posture enables individuals to quantify and conceptualize their health status, thereby helping individuals remain mindful of their health and wellness needs, visualize progress, and maintain the motivation needed to achieve health and fitness goals.

Current vital sign trackers in the consumer market are fairly intrusive, for example, current heart rate monitors often require an individual to strap the monitor around the individual's chest. Many vital sign trackers include just one type of sensor configured to detect one type of vital sign, such as for example, heart rate. Additionally, many vital sign monitors in the consumer market are not very accurate. In the healthcare setting, much more accurate devices are available, but they are often very large devices positionable at a patient's bedside, requiring a connection to an electrical outlet and leads attached to the patient. Attachment to these bedside devices can cause anxiety in patients, and the devices are expensive, not portable and prone to electromagnetic interference (EMI).

Optical fiber sensors have gained increased attention in the research setting, as an alternative to existing vital sign monitors. Optical fiber sensors are chemically inert and resistant to EMI. Moreover, they can be portable and integrated into fixtures, such as mattress pads and cushions. Fixture-integrated devices have numerous advantages over bedside appliances and wearable instruments. For example, fixture-integrated devices allow for a reduction in loose connecting wires or wireless data transmitters between sensors, electronics, and power supplies. This reduction may lead to increased reliability, data quality, and security.

However, optical fiber sensors developed to date have not proven to be suitable alternatives to conventional monitoring systems. For example, in "Optical Fibre Sensors Embedded into Medical Textiles for Healthcare Monitoring," *IEEE Sensor J.* 8 (7), 1215-1222, 2008, Grillet el at proposed integrating a single mode macro-bending fiber sensor into a belt to measure respiratory rate. A macro-bending sensor typically experiences significant light loss due to macroscopic deviations in the fiber's axis from a straight line, resulting in low sensitivity. Such a sensor would be unlikely to detect the subtle movements of the chest wall needed to accurately measure heart rate or ballistocardiogram signals.

In an effort to improve sensitivity, others have proposed alternative approaches for fiber optic sensors. For example, U.S. Pat. No. 6,498,652, Varshneya et al. disclosed a fiber optic monitor that utilizes optical phase interferometry to monitor a patient's vital signs. Optical phase interferometry has several limitations. For example, while Fabry-Perot interferometric sensors and Mach-Zehnder interferometric sensors are sensitive to mechanical vibrations of the body, they are also highly sensitive to mechanical vibrations external to the body, as well as temperature, acoustic waves, magnetic fields, and other environmental, noise. Thus, without proper equipment, interferometer sensors are not suitable for monitoring vital signs due to unreliable performance caused by signal fading and inaccuracies resulting from environmental noise-induced phase change. The equipment needed to filter out the environmental noise includes an expensive phase modulator and coherent optical sources, which add significant cost and complexity and make such sensors impractical for widespread commercial adoption. Other proposed designs have also struggled to balance sensitivity, accuracy, and cost.

Moreover, most fiber optic vital sign sensors being developed are limited to detecting heart rate, breathing rate, and/or macro-movements indicative of changes in body position. A major limitation of many of these sensors is the inability to obtain the highly sensitive ballistocardiography (BCG) waveforms. BCG is a technique used to record vibrations of the body resulting from mechanical activity of the heart. In particular, BCG measures mass movements of the heart and circulating blood generated by forces associated with heart contractions during the cardiac cycle. Historically, BCG waveforms were acquired using an extremely large, suspended table configured to support a patient lying thereon; such a suspended table was heavy, non-portable, and required substantial mechanical maintenance. Due to the cumbersome system required, BCG did not get much attention or use during much of the twentieth century; however, reliable BCG waveforms can provide significant insights into a patient's cardiac health. In addition to revealing a patient's heartbeat unobtrusively, in real-time, BCG waveforms are useful in determining heart rate variability, which is an indicator of stress on a body. Moreover, comparison of BCG and EEG waveforms, in particular, detection of the timing between the R peak of the EEG waveform and the J peak of the BCG waveform reveals beat-to-beat blood pressure changes. Additionally, as described, for example, in E. Pinheiro et al., "Theory and Developments in an Unobtrusive Cardiovascular System Representation; Ballistocardiography," *The Open Biomedical Engineering Journal,* 2010, 4, pp. 201-216, the contents of which is herein incorporated by reference in its entirety, features of BCG waveforms have been found to correlate to, and suggest the presence of, a number of maladies. For example, abnormal BCG waveforms are obtained in individuals having angina pectoris, asymptomatic coronary artery disease, acute myocardial infarction, hypertension, coarctation of the aorta, and mitral stenosis, to name a few.

Despite the clinical value of monitoring BCG, it is not conventionally monitored in a healthcare setting, due to a lack of a suitable detection system. Detecting BCG waveforms requires a level of sensitivity and precision that current sensor designs are lacking. Therefore, a need exists for a physiological parameter monitoring device capable of reliably detecting BCG waveforms. A need also exists for a method of detecting vital signs, including BCG waveforms, which overcomes the limitations of existing methods. Thus, there is a need for new and useful optical fiber vital sign sensors and related methods of use.

SUMMARY

The present disclosure provides new and useful optical fiber sensors and related systems and methods for monitoring BCG waveforms and other vital signs. Various embodiments provided herein overcome one or more of the shortcomings of previously designed fiber optic vital sign monitoring systems.

Various aspects of the disclosure are directed to an optical fiber vital signs sensor and related methods of vital signs detection. The vital signs sensor of various embodiments includes a single layer grid (e.g., mesh) structure and a multimode optical fiber connected to an LED light source. The sensor of various embodiments is configured to achieve high sensitivity and low cost for the monitoring of heartbeat dynamics, breathing patterns, and body movements. The heartbeat dynamics, breathing patterns, and body movement of a patient's body cause micro- or macro-movements that exert forces onto the grid structure. In response, the single layer grid structure applies a continuous force or pressure on the multimode optical fiber. The heartbeat dynamics, breathing patterns, and body movement each thereby exerts a force onto the sensor, which causes micro-bending in the optical fiber of the sensor and thereby modulates the intensity of light transmitted in the multimode optical fiber. By monitoring the optical intensity changes directly coming out of the multimode optical fiber, the system derives the heartbeat dynamics, breathing pattern, and/or other body movement signals.

Because the main sensor structure is composed of a multimode optical fiber, one layer of a grid structure, one LED light source, and one optical signal receiver, the sensor of various embodiments achieves high sensitivity with very low cost. In particular, with these components unchanging across various embodiments, the sensor size and shape can be changed to any size and shape with almost the same cost. In various embodiments of the disclosure, an LED light source and optical signal receiver are used to detect the optical intensity change. No additional optical coupler or optical interference structure is needed to demodulate the signal. Accordingly, the system cost is reduced dramatically compared to interferometry systems. In addition to cost savings, the use of minimum structures achieves high sensitivity. The high sensitivity allows the sensor of various embodiments to detect and provide detailed ballistocardiography waveforms in addition to other vital signs.

One aspect of the disclosure is directed to a sensor for detecting a physiological parameter. The sensor of various embodiments includes a multi-mode optical fiber, an LED light source, an LED driver, a receiver, and a deformer structure. In some embodiments, the multi-mode optical fiber includes an inner core, a cladding layer, and an outer coating, and in the optical fiber, a core diameter is greater than 50% of a cladding diameter. The LED light source is coupled to a first end of the optical fiber and emits light into the first end of the optical fiber. The LED driver is electrically coupled to the LED light source and configured to regulate a power level of the LED light source to regulate an initial intensity of light emitted into the optical fiber. The receiver is coupled to a second end of the optical fiber and configured to sense changes in an intensity of light traveling through the optical fiber. The deformer structure consists of a single mesh layer formed of mesh having openings disposed therein. In some embodiments, a surface area of the openings is between 30% and 60% of a total surface area of the mesh layer. The optical fiber of various embodiments is arranged in a plane in contact with a surface of the deformer structure such that an application of force onto the sensor results in a first portion of the optical fiber bending into an opening of the mesh layer and a second portion of the optical fiber flexing against the mesh. In various embodiments, such deformation of the optical fiber results in light loss through the cladding and thereby modulates the intensity of light reaching the receiver.

In some embodiments, this simplified optical fiber sensor is configured to detect a ballistocardiogram of a patient. The optical fiber sensor may also be used to detect a heart rate, breathing rate, or macro-movements of a patient.

As used herein, in various embodiments, the total diameter of the optical fiber consists of the diameter across the inner core, the cladding layer, and the outer coating.

The mesh layer of some embodiments is formed of interwoven fibers. In some embodiments, a diameter of each interwoven fiber is within 25% of the total diameter of the optical fiber. For example, in some embodiments, a diameter of each interwoven fiber is 75% to 125% of the total diameter of the optical fiber. In some embodiments, the interwoven fibers comprise a polymeric fabric. The mesh layer of some embodiments is configured to uniformly distribute an applied force on the optical fiber. In some embodiments, the opening of the mesh layer is 100% to 300% of the total diameter of the optical fiber. In some embodiments, the opening of the mesh layer is 130% to 170% of the total diameter of the optical fiber.

The optical fiber of some embodiments is arranged in the plane such that a bending diameter of the optical fiber is greater than 1.5 cm. In some embodiments, the optical fiber is at least 10 meters long.

In some embodiments, the LED light source is a low power LED with a 1310 nm or 850 nm central wavelength and 165 nm Full width at half maximum (FWHM). The optical fiber of some embodiments is coupled to the LED light source and the receiver via direct optical fiber connectors without the need for a separate lead fiber. In some embodiments, the optical fiber has a numerical aperture less than or equal to 0.29.

In some embodiments, the sensor also includes a flexible outer cover enclosing the optical fiber and deformer structure. The outer cover of sonic embodiments is formed of silicone.

Another aspect of the disclosure is directed to a method of detecting a physiological parameter. The method of various embodiments includes positioning a sensor under a body, wherein the sensor includes: a multi-mode optical fiber formed of an inner core, a cladding layer, and an outer coating, wherein a core diameter of the optical fiber is greater than 50% of a cladding diameter; an LED light source coupled to a first end of the optical fiber; an LED driver electrically coupled to the LED light source and configured to regulate a power level of the LED light source; a receiver coupled to a second end of the optical fiber; and a deformer structure. The deformer structure consists of a single mesh layer having openings disposed therein, the openings having a surface area between 30% and 60% of a total surface area of the mesh layer. The optical fiber is arranged in a plane in contact with a surface of the deformer structure. The method of various embodiments further includes: detecting, by the receiver, a change in an intensity of light traveling through the optical fiber, wherein the change in light intensity corresponds to fiber deformation caused by a movement of the body, and determining a physiological parameter from the change in light intensity.

The movement of the body may be a macro-movement, such as a change in the body's position, or the movement may be a micro-movement, such as a movement caused by a contraction of the heart, the acceleration of blood through the blood vessels, or the inspiration or exhalation of a breath by the body. In some embodiments, the physiological parameter that is determined by the method is or includes a ballistocardiography (BCG) waveform. In some such embodiments, determining the physiological parameter comprises: determining a BCG waveform of the body, determining an electrocardiogram (EEG) waveform of the body, and calculating a time between an R peak of the EEG waveform and a J peak of the BCG waveform to determine beat-to-beat blood pressure changes.

In some embodiments, determining, the physiological parameter includes: recording the signal detected at the receiver; converting the signal to a digital waveform; filtering out breathing and body movement waveforms from the digital waveform to extract a heartbeat waveform; identifying heartbeat peak values from the heartbeat waveform by separating the heartbeat waveform into a first channel for time domain analysis and into a second domain for frequency domain analysis; and applying a Fast Fourier transform (FFT) in the frequency domain to obtain the heartbeat rate value.

The above-mentioned features, as well as other features, aspects, and advantages of the present technology will now be described in connection with various embodiments of the invention, in reference to the accompanying drawings. The illustrated embodiments, however, are merely examples and are not intended to limit the invention.

DETAILED DESCRIPTION

Figure 1:
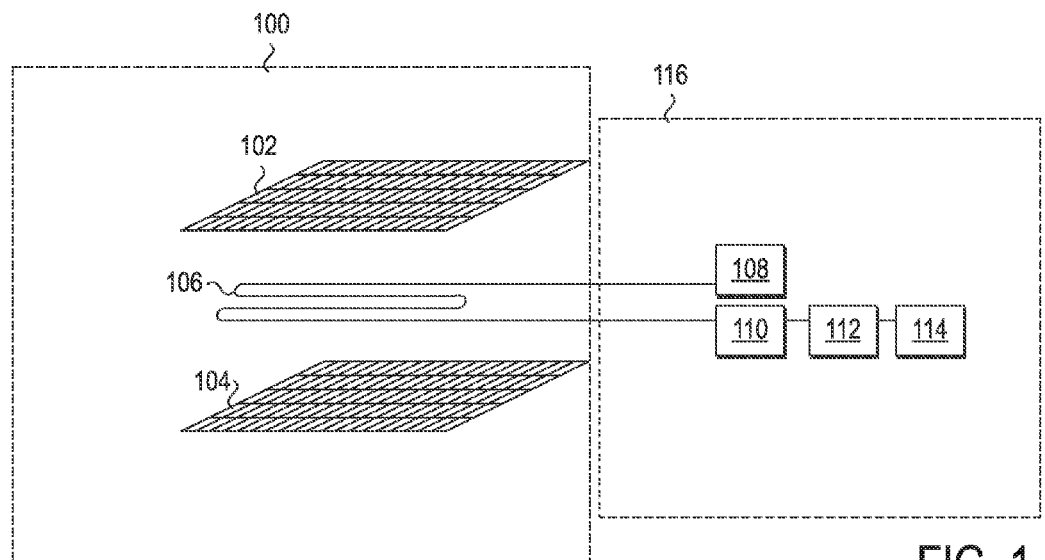
FIG. 1 illustrates a schematic diagram of an intensity-based fiber optic sensor in the prior art.

The provided figures and the following description of certain embodiments of the invention are not intended to limit the invention to these embodiments, but rather, are provided to enable any person skilled in the art to make and use this invention. New optical fiber sensors and related methods of using the optical fiber sensors are disclosed herein. In particular, embodiments utilizing the optical fiber sensors for vital sign monitoring are disclosed.

Optical fibers can be used as sensors to measure strain, temperature, pressure, and other quantities by modifying a fiber so that the quantity to be measured modulates the intensity, phase, polarization, wavelength, or transit time of light in the fiber. There are four categories of fiber optic sensors: intensity-based fiber optic sensors, spectrally based fiber-optic sensors, interferometric fiber-optic sensors, and multiplexed and distributed optical fiber sensors. Two of these sensor types: interferometric fiber-optic sensors and intensity-based fiber optic sensors have shown some promise in detecting vital signs and have been experimented with for such purposes in the prior art.

As described, for example, in U.S. Pat. No. 6,498,652 by Varshneya et al., the disclosure of which is herein incorporated by reference in its entirety, an optical phase interferometry fiber optic sensor can achieve high sensitivity. However, an important challenge lies in the need to differentiate environmental perturbations such as temperature, strain, pressure, etc. from the desired signal. In principle, all environmental perturbations could be converted to optical signals by applying appropriate transducing mechanisms. However, sometimes multiple effects can contribute simultaneously and modify the light in the fiber in a similar manner. For example, changes in temperature, strain, pressure, or any mechanical perturbation could all impact the light in the fiber by changing fiber lengths and refractive indices such that it is difficult to differentiate one perturbation from another. To overcome this obstacle, very expensive, complex, high-maintenance equipment is needed, such as an expensive phase modulator and coherent optical sources. Accordingly, the high cost, complexity, and need for continued maintenance have limited the commercial use of such sensors for health and wellness monitoring.

Intensity-based fiber optic sensors are far simpler sensors, capable of functioning with a simple light source (e.g., a low power LED) and a simple detector without the need for phase modulators. However, it has proved challenging for those in the field of optical fiber sensing to develop a simple, low cost intensity-based fiber optic sensor that also has sufficiently high sensitivity to make this form of sensor a viable, practical option. Many types of optical intensity sensors have been developed in an effort to create one that has sufficient sensitivity. One type of intensity-based fiber optic sensor, in particular, has shown some promise: the microbending optical fiber sensor. Microbending optical fiber sensors rely on microbending of the fiber, resulting, for example, from an externally applied force or pressure, to induce light intensity modulation. Intensity modulation induced by microbending in multimode fibers is considered as a transduction mechanism for detecting environmental changes such as pressure, temperature, acceleration, and magnetic and electric fields. Microbending of the fiber locally results in intensity modulation of the light propagating through an optical fiber. Microbending has been studied since the 1970s. However, there has yet to be industry standard specifications or test methods, almost 40 years later. That is because there are so many parameters that affect microbending fiber optic performance, including optical fiber length, reflective index, and optical core and cladding diameter, and deformer stillness, material, periodicity, diameter, etc. Moreover, as described in detail below, past researchers have failed to develop a microbending optical fiber sensor structure that is both sensitive and reliable enough to consistently and accurately detect BCG waveforms outside of the laboratory.

Microbending Optical Fiber Sensor

FIG. 1 illustrates a microbending optical fiber sensor in the prior art. The sensor 100 includes a dual deformer structure comprising a top mesh layer 102 and a bottom mesh layer 104, which together sandwich the optical fiber 106. A first end of the optical fiber 106 is connected to a light source 108, and a second end of the optical fiber 106 is connected to a signal receiver 110. The signal receiver is further coupled to a signal amplifier 112 and a signal processing unit 114. Together, the electronic components of the light source 108, signal receiver 110, amplifier 112, and signal processing unit 114 form the detection unit 116. A similar microbending optical fiber sensor is described, for example, in US Publ. No. 201210203117 by Chen, the disclosure of which is herein incorporated by reference in its entirety. Chen discloses the simultaneous measurement of breathing rate and heart rate using a microbending multimode fiber optic sensor. A similar structure was described by Chen et al. in "Portable fiber optic ballistocardiogram sensor for home use," 2012, vol. 8218, p. 82180X-82180X-7, the disclosure of which is herein incorporated by reference in its entirety.

It was widely believed that a dual deformer structure, such as the one described in Chen, was needed in order to produce a microbending response large enough to make a body's micro-movements, indicative of physiological parameters such as heart beat and breathing, detectable. It was assumed and taught that a mesh structure needs to be placed on each side of the optical fiber and aligned such that the fibers of one mesh layer are directly centered within the openings in the other mesh layer. Such a structure creates pressure points on both a top side and a bottom side of the optical fiber, which facilitates deformation of the fiber.

Equations have been developed to explain this phenomenon and to identify the ideal size and placement of the dual deformer structures. Such a prior art dual deformer structure is shown, for example, in FIGS. 2A and 2B.

Figure 2A:
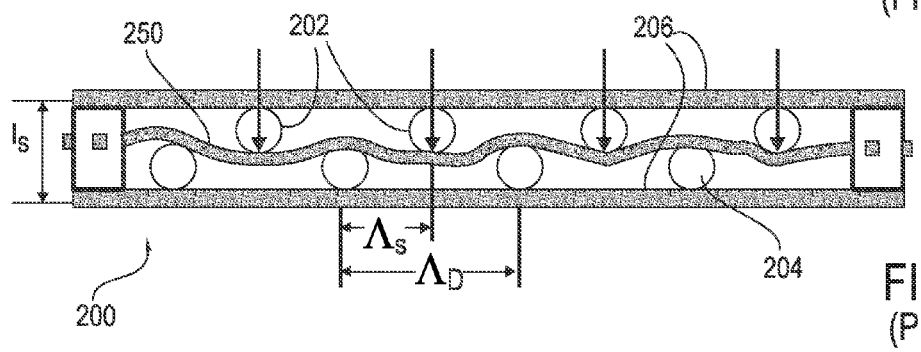
FIGS. 2A and 2B illustrate schematic cross-sectional views of an intensity-based fiber optic sensor in the prior art.
Figure 2B:
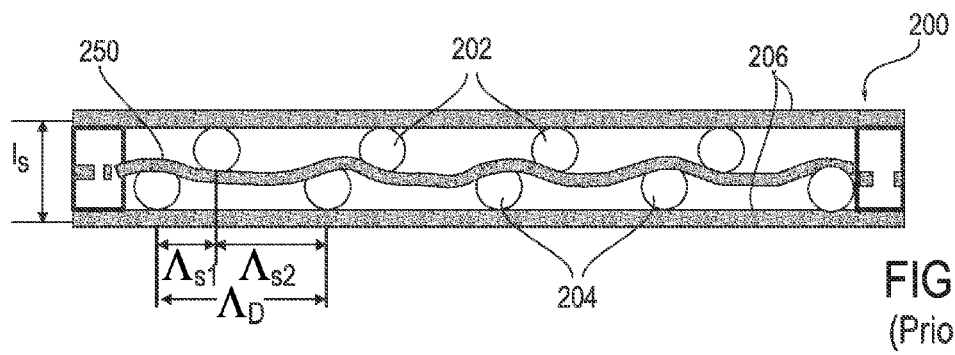

As illustrated in FIG. 2A and FIG. 2B, an optical fiber 100 is placed within a dual deformer structure 200 formed of a top layer of interwoven fibers 202 and a bottom layer of interwoven fibers 204. The optical fiber 100 is sandwiched between the two layers of the dual deformer structure 200. A cover 206 surrounds the dual deformer structure. The total height of the dual deformer structure is $l_s$. The intra-layer periodicity of the deformer, meaning the distance between adjacent, parallel fibers in a mesh layer, is $\Lambda_D$. The inter-layer periodicity of the deformer, which is the horizontal distance between fibers of the upper and lower deformer, is $\Lambda_s$. In a dual deformer structure, an outside applied force is concentrated on the optical fiber 100 at the locations of the mesh fibers. In order for force to be applied evenly onto the optical fiber 100, $\Lambda_s$ must be half of $\Lambda_D$. In order to achieve the greatest bending, and thus, the highest sensitivity, $\Lambda_s$ must be half of $\Lambda_D$.

When a lateral displacement misaligns the upper and lower mesh layers of the deformer 200, the applied force is no longer applied evenly onto the fiber 100 and $\Lambda_s$ is no longer uniform. In this situation, as shown in FIG. 2B, $\Lambda_s$ is replaced by $\Lambda_{s1}$ (left side distance between fibers of upper mesh and lower mesh layers) and $\Lambda_{s2}$ (right side distance between fibers of upper mesh and lower mesh layers).

For a graded index, micro-bending fiber, the optimum intra-layer periodicity $\Lambda_D$ of the deformer is obtained from the following equation:

$$\Lambda_D = \frac{2\pi a n_0}{N.A.}$$

as disclosed, for example, by Lagakos et al. in "Microbend fiber-optic sensor," Appl. Opt., vol, 26, no. 11, pp. 2171-2180, June 1987, the disclosure of which is herein incorporated by reference in its entirety. In the equation, a is the core radius, $n_0$ is the refractive index of the core and N.A. is the numerical aperture of the fiber. Lagakos arrives at the following values for the tested fiber: a=47.5 um, N.A.=0.13 and $n_0$=1.458 and concludes that an intra-layer periodicity ($\Lambda_D$) of 3.35 mm achieves the highest microbending sensitivity for a pressure sensor. Chen uses the same equation in US Publ. No, 2012/0203117, arriving at a periodicity of 1.68 mm.

In a dual deformer structure, the equation of intra-layer periodicity $\Lambda_D$ is used to maximize the performance of a pressure sensor by maximizing light loss under a given pressure force. The purpose is to achieve the highest fiber bending loss. In other words, to achieve the highest $\Delta X$.

$$k_{dual}\Delta X = \Delta F_{bending}$$

In a dual deformer structure, $$k_{dual}^{-1} = \frac{\Lambda_D^3}{3E_y I_{bend}}$$

where $E_y$ is Young's modulus, $I_{bend}$ is the bending moment of inertia, and $\Lambda_D$ is the intra-layer periodicity. The bending moment of inertia ($I_{bend}$) characterizes the stiffness of an elastic member, and for an object with a circular cross-section, such as an optical fiber, $I_{bend}$ is given by the equation:

$$I_{bend} = \frac{\pi D_{fiber}^4}{64}$$

where $D_{fiber}$ is the fiber diameter.

In dual deformer structures, the optical fiber 250, which is sandwiched between a pair of deformer mesh layers 202, 204, is constrained to bend in a regular pattern with periodicity $\Lambda_D$. The deformer 200, in response to an appropriate environmental change $\Delta E$, applies a force $\Delta F$ to the optical fiber 250 causing the optical fiber to deform by an amount $\Delta X$. The transmission coefficient for light propagating through the bent fiber is in turn changed by an amount $\Delta T$ so that:

$$\Delta T = \left(\frac{\Delta T}{\Delta X}\right) D \Delta E \quad (1)$$

where $$D\Delta E = \Delta X \quad (2)$$

Here D is a constant, which depends on the environment change ΔE. In terms of the applied force ΔF, equation (1) becomes $$\Delta T = \left(\frac{\Delta T}{\Delta X}\right) \Delta F \left(K_f + \frac{A_s Y_s}{l_s}\right)^{-1} \quad (3)$$

where $K_f$ is the bend fiber force constant and $A_s Y_s/l_s$ is a force constant. Here $A_s$, $Y_s$ and $l_s$ are: a cross sectional area, Young's modulus, and height of the dual deformer structure, respectively. The change in the photo detector output signal is thus used to detect the original environment perturbation ΔE.

Depending on the construction of the deformer, various environmental parameters can, in principle, be sensed. The deformer converts the change in the environmental parameter ΔE to a force ΔF on the bent fiber, according to the equation: ΔF=ΔE*C. For the generic dual deformer, the parameter C can be expressed as a simple function of deformer parameters for the various environmental sensors. For a pressure sensor, C is simply equal to the area of the deformer plate $A_p$, thus equation (3) becomes $$\Delta T = \frac{\Delta T}{\Delta X} \cdot A_p \left(K_f + \frac{A_s Y_s}{l_s}\right)^{-1} \Delta P \quad (4)$$

where ΔP is the change in pressure. Thus a high sensitivity pressure sensor should have a constant $A_s Y_s/l_s$ small enough that the effective compliance is determined by the compliance of the optical fiber, which is itself quite large. In this case, equation (4) becomes:

$$\Delta T = \frac{\Delta T}{\Delta X} \cdot A_p K_f^{-1} \Delta P \quad (5)$$

Equation (5) can be written in the form of equation (1), where ΔE represents the environmental change, e.g., pressure and temperature, and D is a constant identified in the above equations for the various environmental sensors. Under an environmental perturbation ΔE, the photo detector signal output $i_s$ is given as $$i_s = \frac{qeW_0}{hv}\left(\frac{\Delta T}{\Delta X}\right) D \Delta E \quad (6)$$

where h is Planck's constant, v is the optical frequency, q is the detector quantum efficiency, e is the electron charge, and $W_0$ is the input optical power. Assuming a shot-noise-limited detection system, the mean square photo-detector noise is given as $$i_s^2/i_N^2 = \left(\frac{qW_0}{hv}\right)\left(\frac{\Delta T}{\Delta X}\right)^2 D^2 (\Delta E)^2 (2T\Delta F)^{-1} \quad (7)$$

The smallest signal that can be detected is given for the condition S/N=1, which yields $$\Delta E_{min} = D^{-1}\left(\frac{\Delta T}{\Delta X}\right)^{-1} \sqrt{\frac{2Thv\Delta f}{qW_0}} \quad (8)$$

The first factor is specific to the particular design of the environmental sensor; the second two factor, however, is general and applies to all environmental microbending sensors. A generic microbending sensor can be defined as one which measures ΔE as defined by Eq. (2). Then combining Eqs. (2) and (8) yields $$\Delta X_{min} = \left(\frac{\Delta T}{\Delta X}\right)^{-1} \sqrt{\frac{2Thv\Delta f}{qW_0}} \quad (9)$$

which provides the minimum amount the optical fiber must bend in order to detect an environmental perturbation. Based on these results, the minimum detectable environmental changes ΔE can be determined. According to Chen in US Publ. No, 2012/0203117, the optical fiber sensor with the dual deformer structure was sensitive enough for heart beats and breathing to be detectable environmental perturbations. Chen further suggests in "Portable fiber optic ballistocardiogram sensor for home use," that such a structure may be sufficiently sensitive to detect BCG waveforms. However, as mentioned above, the sensitivity of the sensor having, a dual deformer structure is dependent on $\Lambda_s$ being equal to half of $\Lambda_D$. When $\Lambda_s$ is not half of $\Lambda_D$, the predesigned periodicity of the microbend deformer $\Lambda_D$ will not be the optimized value necessary to achieve the best performance. Unless the upper and lower mesh layers are able to remain in proper alignment, the dual deformer style optical fiber sensor of Chen lacks sufficient sensitivity and reliability to monitor BCG waveforms.

It may be possible to maintain proper alignment of the upper and lower layers of mesh with the addition of specialized support structures; however, doing so greatly increases the cost and complexity of the system, which makes the system impractical for consumer applications such as long-term vital sign monitoring systems.

Without the costly support structures, the dual deformer structure is not suitable for detecting BCG waveforms in practice outside of a laboratory. While the two mesh layers of the dual deformer may begin in an aligned configuration and generate sensitive and reliable results in a laboratory, when used by consumers, the slipping of one deformer layer relative to the other deformer layer often results. In real applications of vital sign monitoring, where an individual is sitting or lying on an optical fiber sensor. There are pressures and forces of different directions routinely applied on the sensor. This pressure or force can be divided into vertical and horizontal components. The vertical component is the component that results in a downward force on the optical fiber, and accordingly, microbending of the fiber. However, shifts in body weight will almost always have a horizontal component as well. The horizontal component caused by a patient moving induces a force that may change the periodicity between the mesh layers. The change in $\Lambda_s$ and $\Lambda_D$ significantly reduces the sensitivity of the system since the greatest amount of microbending will no longer be achievable. Moreover, the change in $\Lambda_s$ and $\Lambda_D$ significantly reduces the reliability of the system since the placement of the forces on the optical fiber become unpredictable all calculations performed by the signal processor in the system are based on the assumption that $\Lambda_s$ and $\Lambda_D$ have remained constant. Thus, as the sensor system is used, the dual deformer style optical fiber sensors become unreliable and sensitivity decreases. This is not acceptable for commercial applications. Accordingly, a different approach and different structure is needed.

Single Deformer Sensor

As stated above, it has previously been believed that a dual deformer structure was necessary to achieve an amount of microbending sufficient to detect vital signs. It is the present author's surprising discovery that an amount of microbending sufficient to detect vital signs, including BCG waveforms, can be achieved using a single deformer structure, if the optical fiber sensor utilizes includes an optical fiber having specific properties. As described further herein, a specific relationship has been discovered between characteristics of the optical fiber and the single mesh layer that make such a system conducive to reliable, sensitive results.

Figure 3:
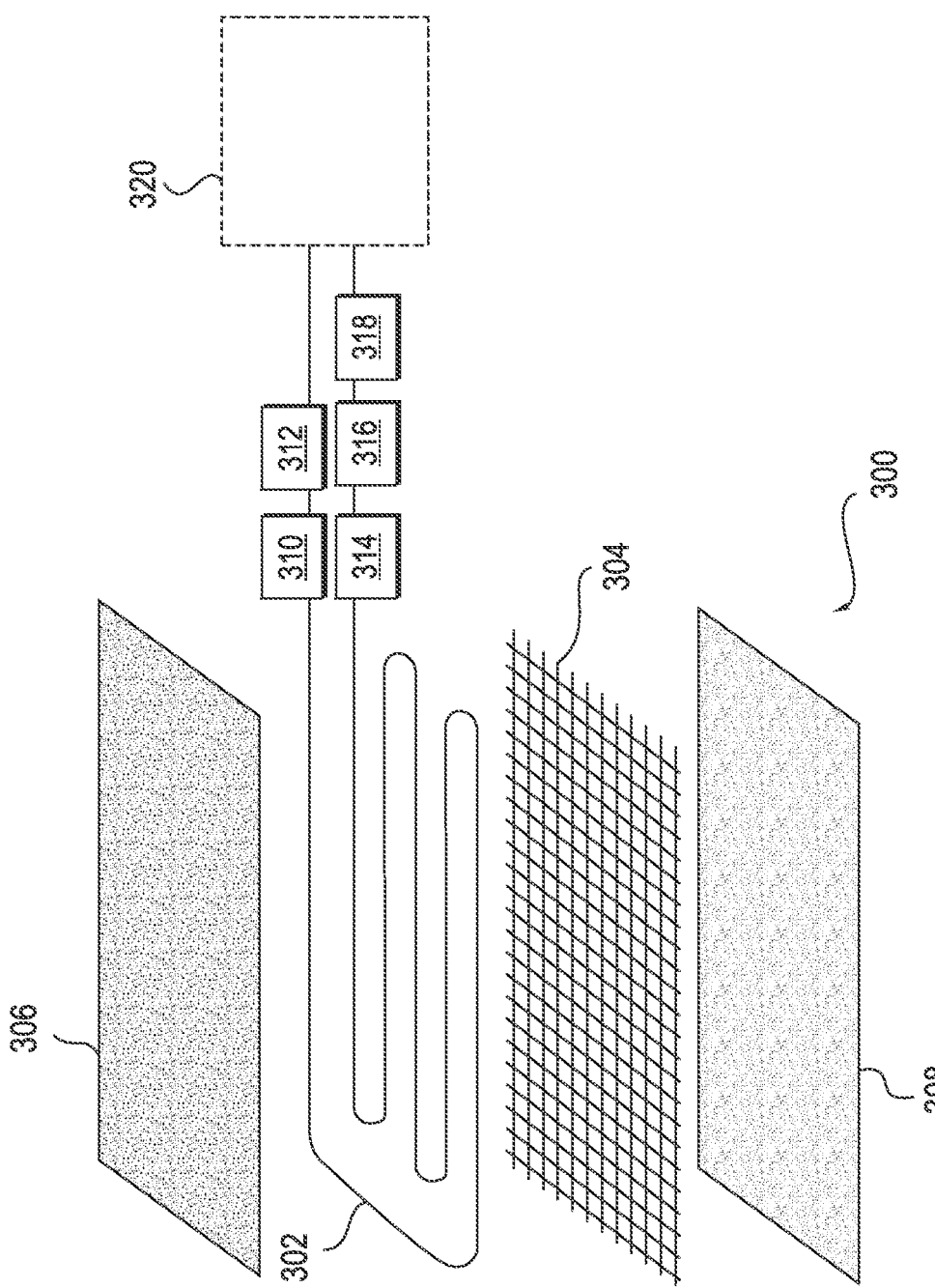
FIG. 3 illustrates a schematic diagram of one embodiment an intensity-based fiber optic sensor in accordance with the teachings of the present disclosure.

FIG. 3 illustrates one embodiment of the sensor structure in accordance with the present disclosure. The sensor 300 includes a multimode optical fiber 302 and a single layer of mesh 304, which are together held between a front cover 306 and a back cover 308 to form a sensor sheet. One end of the optical fiber 302 is connected to a light source 310, which in a preferred embodiment, is an LED light source operated by an LED driver 312. Another end of the optical fiber 302 is connected to an optical signal receiver 314. An amplifier 316 is coupled to the optical signal receiver 314 to amplify the optical signal large enough for processing by an analog-to-digital converter 318. The optical and electrical components (310, 312, 314, 416, 318) are connected to a control and processing module 320. The provided sensor is configured for optical intensity monitoring. Input light is generated from the light source 310 and transmitted to optical multimode fiber 302. In the presence of an external force generated by body weight, heartbeat, respiration, or other physiological parameter, this force is uniformly distributed on the fiber 302 and mesh structure 304. These forces microbend the multimode fiber, and some light leaks out due to the microbending effect. Optical signal receiver 314 receives the residual light and changes in the amount of light intensity are processed and determined by the control and processing module 320.

Unlike sensors of the prior art which use two microbending deformer layers, the sensor of the present disclosure uses a deformer structure formed of a single layer of mesh.

Figure 4A:
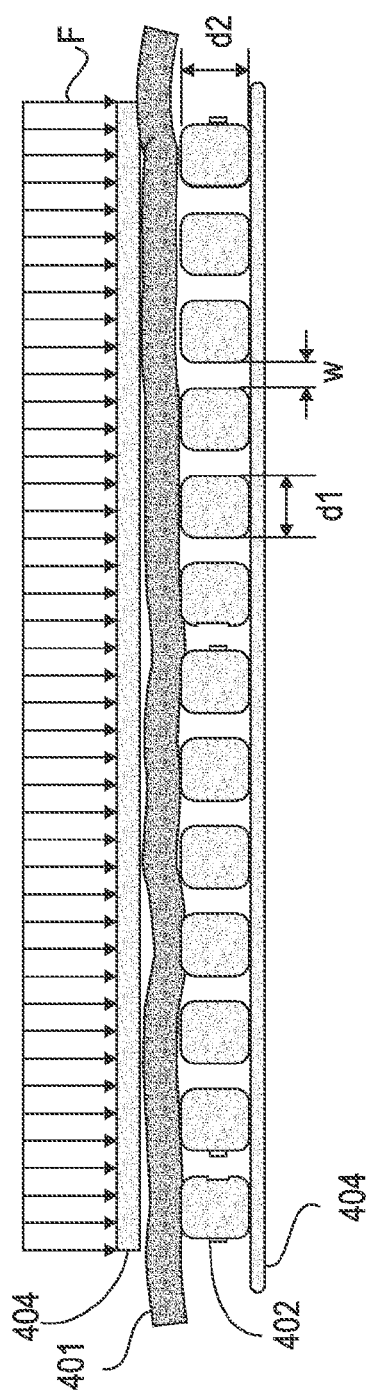
FIG. 4A illustrates a schematic cross-sectional view of one embodiment of an intensity-based fiber optic sensor in accordance with the teachings of the present disclosure.
Figure 4B:
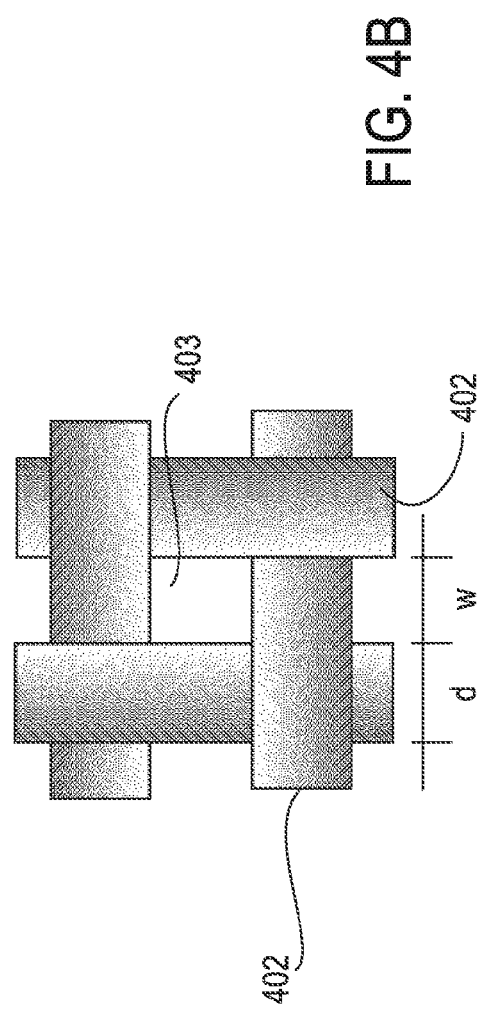
FIG. 4B illustrates a schematic top view of one embodiment of a mesh deformer structure, such as the mesh deformer structure found in the intensity-based fiber optic embodiment of FIG. 4A.

FIGS. 4A and 4B illustrate one embodiment of the deformer structure according to the present disclosure. In the present deformer structure, one single layer of mesh 402 is used to achieve micro-bending on a multimode fiber 401. As used herein, mesh may refer to any suitable material having a repeating pattern of through holes. In some embodiments, the mesh is formed of interwoven fibers, such as, for example, polymeric fabric fibers, natural fabric fibers, composite fabric fibers, metallic fibers, or other fibers. In this mesh layer, $a_o$ is the open area of the through holes 403. The diameter or width of each mesh fiber in the x direction is $d_1$. The diameter or height of each mesh fiber in the z direction is $d_2$. The width of each mesh opening is w. When an outside force caused by body weight, a heartbeat, respiration, or other physiological parameter is applied on the sensor, this force is uniformly distributed onto an upper cover 404 and the multimode optical fiber 100.

In the new sensor structure of the present disclosure, a mesh structure 402, such as a polymeric open mesh fabric, is used as the single layer deformer, and a cover material 404, such as silicone, is configured to surround the multimode optical fiber 401 and the mesh layer 402 to distribute uniformly any force applied on the sensor.

In the one layer deformer structure of the disclosure, an applied outside force is uniformly distributed along the optical fiber length. The force per unit length is denoted by $F_{dist}$, and the amount of deformation is;

$$k_{distributed} \Delta X = \Delta F_{dist}$$

where $$k_{distributed}^{-1} = \frac{\Lambda_L^4}{8 E_y I_{bend}}$$

and where $E_y$ is Young's modulus, $I_{bend}$ is the bending moment of inertia, and $\Lambda_D$ is the length of period. The bending moment of inertia characterizes the stiffness of an elastic member, and for an object with a circular cross section, such as an optical fiber, it is given by:

$$I_{bend} = \frac{\pi D_{fiber}^4}{64}$$

where $D_{fiber}$ is the fiber diameter. So, $$k_{distributed}^{-1} = \frac{8 \Lambda_L^4}{E_y \pi D_{fiber}^4}$$

In sensors utilizing single layer deformers, $$\Lambda_L = d_1 + w$$

Combining this information together yields the amount the optical fiber will bend in response to an application of force in a structure having a single layer deformer structure. In particular:

$$\Delta X = (\Delta F_{dist}) \frac{8(d_1 + w)^4}{E_y \pi D_{fiber}^4}$$

As shown, a sensor utilizing a deformer structure made of only one layer of mesh has different bending parameters than a dual deformer structure. In the currently provided embodiments, each of which employ a single layer deformer structure, the amount of bending depends not only on the applied force but also the diameter of the optical fiber, the diameter of the mesh fiber, and the size of the openings in the mesh. By balancing these parameters, a sensor can be created that bends a sufficient amount to detect light loss in response to the force of a micro-movement of a body on the sensor.

Relationship Between Mesh Layer and Optical Fiber Parameters

It is the unexpected discovery of the present authors that a more reliable and sufficiently sensitive sensor can be created using the deformer structure described above, if the size of the deformer structure is appropriately selected and paired with an appropriately sized optical fiber. In particular, it was found that eliminating the second mesh layer significantly reduces the noise and error that results from the two mesh layers sliding, relative to each other. Moreover, it was found that an amount of microbending sufficient to achieve detectable light loss can be obtained when the deformer only includes one mesh layer, if a specialized multimode optical fiber is used. It is both the characteristics of the optical fiber and their relationship to characteristics of the mesh layer that result in sufficient microbending.

For example, the specialized multimode optical fiber of the present disclosure has a large core diameter configured to receive and transmit a relatively large amount of light. Moreover, the specialized multimode optical fiber is a highly flexible bare fiber, which includes the optical fiber core, outer cladding, and a coating layer, but does not include a tight buffer layer. Rather than including a tight buffer layer, additional protection to the optical fiber and the system is provided by the highly flexible cover 404, which surrounds both the fiber and the deformer structure.

It is a discovery of the present authors that a bare multimode optical fiber will bend a sufficient amount in response to physiological parameters of interest if an appropriate ratio of core to cladding is selected, if the mesh layer of the deformer is an appropriate size for the optical fiber, and if an appropriate power level is used.

The optical fiber sensors of the various embodiments disclosed herein each have a novel configuration that enables sufficient microbending to be achieved using a deformer having only one mesh layer. Each of the embodiments described below is configured to microbend a sufficient amount to monitor BCG waveforms, heart rate, breathing rate, and other physiological parameters.

Figure 5:
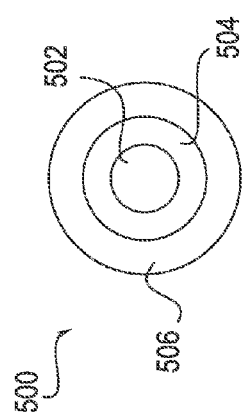
FIG. 5 illustrates a schematic cross-sectional view of one embodiment of a multi-mode optical fiber in accordance with the teachings of the present disclosure.

A multimode optical fiber of the current disclosure is provided in FIG. 5. As shown, the optical fiber 500 is formed of an inner core fiber 502, a cladding layer 504, and an outer coating 506. In various embodiments, the inner core 502 has a diameter equal to or greater than 50% of the diameter of the cladding layer 504. In preferred embodiments, the diameter of the inner core 502 is greater than 50% of the diameter of the cladding layer 504. In some embodiments, the diameter of the inner core 502 is substantially greater than 50%, for example, at least 75%, 80%, or 90% of the diameter of the cladding layer 504. As used herein, the diameter of the inner core refers to the diameter across the inner core; the diameter of the cladding layer refers to the diameter across the entirety of the cladding layer and the inner core; and the diameter of the outer coating or the total diameter of the optical fiber refers to the diameter across the entirety of the outer coating, the cladding layer, and the inner core. In some embodiments, the diameter of the cladding layer is 125 µm. In some such embodiments, the inner core has a diameter of at least 62.5 µm. In some embodiments, the inner core has a diameter greater than 62.5 µm. For example, in some such embodiments, the inner core has a diameter of at least 80 µm, at least 90 µm, at least 100 µm, or at least 110 µm. In one embodiment, the optical fiber has an inner core diameter of 100 µm and a cladding layer diameter of 125 µm. In various embodiments, an outer coating adds additional width to the optical fiber. In some such embodiments, the total diameter of the optical fiber is 250 µm. In another set of embodiments, the optical fiber has a cladding layer diameter of 250 µm. In some such embodiments, the inner core has a diameter equal to, or greater than, 125 µm. In some such embodiments, the inner core has a diameter greater than 150 µm, greater than 160 µm, greater than 170 µm, greater than 180 µm, greater than 190 µm, greater than 200 µm, greater than 210 µm, or greater than 225 µm.

In various embodiments of the disclosed optical fiber sensor, the mesh layer of the deformer is configured such that the open area between fibers $a_o$ is between 30% and 60% of the total mesh surface area. In some embodiments, the through-holes of the mesh layer are sized to receive an entire diameter of the optical fiber. In some embodiments, the through-holes of the mesh layer are sized to receive the width of an optical fiber structure, including the optical fiber and surrounding outer coating. Thus, in some embodiments, the opening of the mesh layer is 100% to 300% if the total diameter of the optical fiber. In some embodiments, the opening of the mesh layer is 130% to 170% of the total diameter of the optical fiber.

In still another embodiment, the mesh opening w is preferably selected to be between 200 and 750 µm. In an alternative embodiment, the mesh opening is up to three times greater than the total optical fiber diameter.

In some embodiments, a diameter of each mesh fiber is within 25% of the total diameter of the optical fiber. In some embodiments, each mesh fiber has a diameter equal to 75% to 110% of the total diameter of the optical fiber. In some embodiments, each mesh fiber has a diameter greater than 70% and less than 100% of the total diameter of the optical fiber. In some embodiments in which the optical fiber has a cladding layer diameter of 125 µm and a total diameter of 250 um, a diameter of each mesh fiber is selected to be in the range of 180 to 240 µm.

In a preferred embodiment, the multimode optical fiber has a numerical aperture less than or equal to 0.29 µm, a 100 µm core diameter, a 125 µm cladding layer diameter, and a 250 µm total diameter. In some embodiments, for example, in this preferred embodiment, the mesh fiber has a diameter between 180 and 240 µm. In some embodiments, for example, in this preferred embodiment, the mesh opening w is sized between 330 and 375 µm.

The optical fiber may be any length suitable for the area of detection. In some embodiments, the sensor includes at least 10 meters of multimode optical fiber. In some such embodiments, the multimode optical fiber is arranged along a plane and wound, coiled, or snaked along the plane. Macrobending effects can significantly decrease the microbending effect and are preferably avoided. Macrobending losses are high in 0.29 micron numerical aperture fiber for bends of less than 1.5 cm in diameter. Thus, in some embodiments, a bending diameter greater than 1.5 cm is used when laying the optical fiber on the plane. In some embodiments, the optical fiber is arranged directly on the mesh layer.

Various embodiments of the present disclosure are directed to a sensor configured to achieve high sensitivity and reliable performance at low manufacturing cost and complexity.

Fiber sensor leads also affect the sensitivity. In some embodiments, a lead fiber is needed to couple the light from the light source to the fiber, and another lead fiber is needed to connect to the detector. In such embodiments, the core sizes of the lead and sensing fibers should be approximately the same to minimize fusion loss. In preferred embodiments of the disclosure, the need for separate fiber sensor leads is eliminated by directly connecting the multimode fiber to the electronic and optical components.

In a preferred embodiment, a low power, low cost 850 nm or 1310 nm central wavelength LED with 165 nm Full width at half maximum (FWHM) is used as light source. A photo detector range (770 nm to 860 nm or 1100 nm to 1650 nm) photo detector with 0.4 A/W responsivity is used as the optical receiver. In other embodiments, any suitable LED light source or other low power, low cost light source may be used. Additionally, in other embodiments, any suitable light receiver may be used.

Electro-Optic Unit and Controller

Figure 6:
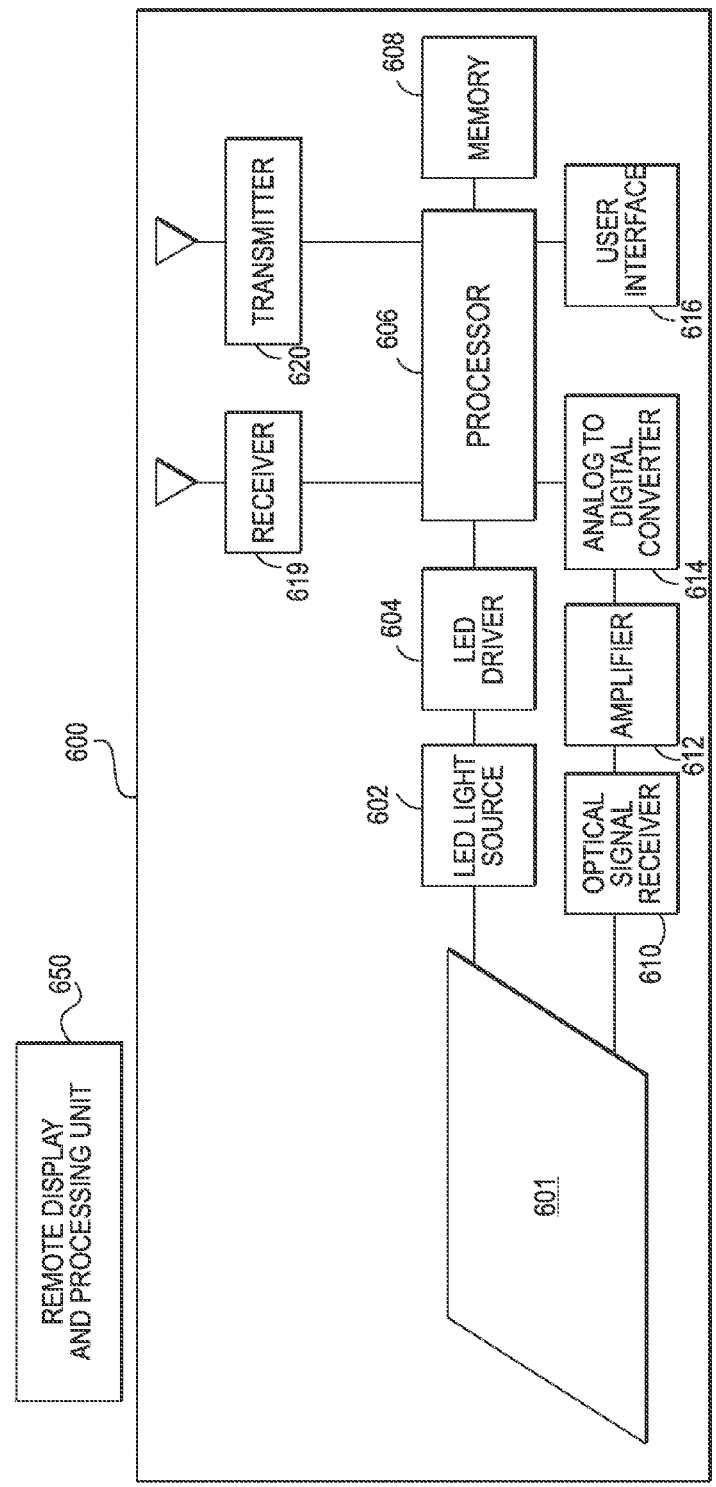
FIG. 6 illustrates a block diagram of one embodiment of an intensity-based fiber optic sensor system in accordance with the teachings of the present disclosure.

FIG. 6 illustrates a block diagram of an optical intensity microbending fiber sensor system 600 for detecting and displaying physiological parameters of a body. In the illustrated embodiment, a low cost fiber sensor sheet 601 is provided, which may include any embodiment of a top cover, multimode optical fiber, mesh layer, and back cover described elsewhere herein, for example, in relation to FIGS. 3-5. A light source 602 supplies optical radiation to the multimode fiber embedded within sensor sheet 601. The light source 602 may be a broadband optical source 165 nm, FWHM LED light source 1310 nm, or any other suitable light source. An LED driver 604 drives the optical light source 602 and is controlled by a processor 606 executing instructions stored in memory 608. The other end of the multimode fiber is connected to the optical signal receiver 610, which is comprised of a photo detector. In some embodiments, the photo detector has a detection range from 1100 nm to 1650 nm and 0.4 A/W responsivity. The optical signal receiver 610 converts the optical intensity into an analog electrical signal, which is then amplified by an electrical amplifier 612. An analog-to-digital converter 614 converts the analog electrical signal into a digital signal that is transmitted to and processed by the processor 606. In some embodiments, a user interface 616 may be provided and used by a user to control some or all of the device's functionality. The digital signal is optionally processed by the processor 606, and the raw or processed digital signal is transmitted to a remote system 650 to display and further process the signal. This remote system 650 can be a smart phone, tablet, other mobile computing device, or other computer with appropriate communication capabilities. In some embodiments, the raw or processed digital signal is transmitted to the remote system 650 wirelessly, for example, via radiofrequency (RF) signals utilizing a transmitter 620. The transmitter 620 of some embodiments is configured to transmit Wi-Fi®, Bluetooth®, or other RF signals. In some embodiments, the remote system 650 can in turn control and activate the sensor system 600 by sending signals to a receiver 618, which may be, for example, an RF signal receiver.

The processor 606, the memory 608, and the signal processing components (e.g., the amplifier 612 and the analog-to-digital converter 614) may include a combination of hardware and software, which is configured to control the frequency, intensity, and/or activation of the light emitted by the light source, and which is further configured to convert the signals received from the signal receiver into meaningful data. One skilled in the art will appreciate that many different structural components and architectures may be used to achieve such functionality. Although illustrated separately, it is to be appreciated that the various blocks of the system need not be separate structural elements. For example, in the processor in data communication with the memory may be embodied in a single chip or two or more chips.

The processor 606 may be a general purpose microprocessor, microcontroller, a digital signal processor (DSP), a field programmable gate array (FPGA), an application specific integrated circuit (ASIC), or other programmable logic device, or other discrete computer-executable components designed to perform the functions described herein. The processor may also be formed of a combination of computing devices, for example, a DSP and a microprocessor, a plurality of microprocessors, one or more microprocessors in conjunction with a DSP core, or any other suitable configuration.

In various embodiments, the processor 606 is coupled, via one or more buses, to the memory 608 in order to read information from and write information to the memory 608. The processor 606 may additionally or alternatively contain memory 608. The memory 608 can include, for example, processor cache. The memory 608 may be any suitable computer-readable medium that stores computer-readable instructions for execution by computer-executable components. For example, the computer-readable instructions may be stored on one or a combination of RAM, ROM, flash memory, EEPROM, hard disk drive, solid state drive, or any other suitable device. In various embodiments, the computer-readable instructions include software stored in a non-transitory format. The processor 606, in conjunction with the software stored in the memory 608, executes an operating system and stored software applications. Various methods described elsewhere herein may be programmed as software instructions stored in the memory 608.

The user interface 616 may include a user input device, such as a button, a toggle, a switch, a touchscreen, or a keypad, and/or an output device such as a display screen, light display, audio output, or haptic output. The user input device may be configured to receive user commands to power the sensor on and off. In some embodiments, data about a user may also be input via the user input device.

The receiver 618 of various embodiments receives and demodulates data received over a communication network. The transmitter 620 prepares data according to one or more network standards and transmits data over a communication network. In some embodiments, a transceiver antenna acts as both a receiver and a transmitter. Additionally or alternatively, in some embodiments, the system includes a databus for sending and/or receiving data to one or more remote components via a wired connection.

In some embodiments, the processor 606 is configured to compute applied forces from changes in propagated light intensity. In some embodiments, the processor 606 is configured to compute one or more vital signs of a user from the data on applied forces. In some embodiments, some or all such data is transmitted via a wired or wireless connection to the remote system 650 for storage and/or display.

Figure 7A:
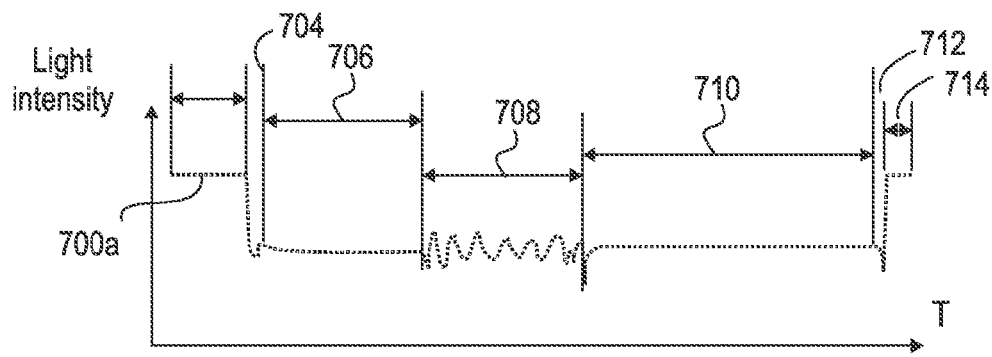
FIGS. 7A-7D illustrate one example of as raw digital signal, a combined heartbeat and breathing waveform, a heartbeat waveform, and a breathing waveform, respectively acquired from an embodiment of the intensity-based fiber optic sensor system of the present disclosure.
Figure 7B:

In sonic embodiments, the processor 606 is configured to extract a heartbeat waveform, respiration waveform, and movement waveform from the raw signal. One example of such signal extraction is shown in FIGS. 7A-7D. The raw signal 700a is received at the signal processing components. As illustrated in FIG. 7A, in time window 702, the light intensity is at the highest level, which means there is no user on the sensors. There is no light loss due to the bending of the fiber. Time window 704 represents the moment when a user sits, stands, or lays on the sensor, which makes the received light intensity drop significantly in a very short period; the signal then maintains a consistently low level as in 706. At illustrated time windows 706 and 710, the user is sitting or lying on the sensor without moving. During such times, the light intensity is kept within a relatively narrow range. By amplifying the signal in time windows 706 or 710, a detailed signal is detectable, which includes a heartbeat waveform and respiration waveform, as shown in FIG. 7B as signal 700b. When a user remains sitting, standing, or lying on the sensor but shifts positions or moves, a signal such as the signal shown in time window 708 results. As shown, during such times, the optical intensity changes in a range larger than the intensity change caused by respiration and heartbeats but in a range much smaller than the intensity change caused by complete addition or removal of the body from the sensor. The processor 606 of some embodiments is configured to identify the movement frequency and amplitude from this signal. The time window 712 depicts the signal as the user leaves the sensor. The received light intensity then recovers to the original level, as shown in 714.

Figure 7C:
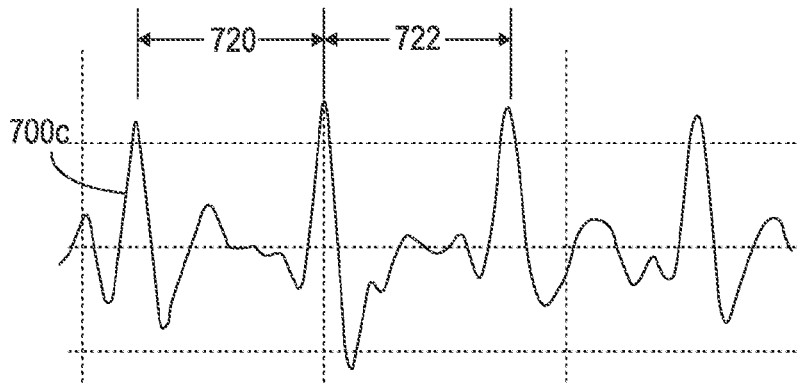

To extract the heartbeat waveform, also called a ballistocardiography (BCG) waveform, from such a signal, the processor 606 may combine different stage high pass and low pass filters to remove noise. The BCG waveform 700c, shown for example in FIG. 7C, provides detailed information for every heartbeat. The BCG waveform acquired by the present system has very clear H, I, J, K, L, and M peaks. By identifying a heartbeat peak value, time differences between adjacent heartbeats 720, 722 can be computed. The processor 606 may calculate heart rate by gathering all the time differences and transferring them into a frequency in time domain. The processor 606 may calculate heart rate variability by calculating the average time difference between adjacent peaks over a certain time period. The processor 606 may determine a stress level, such as a mental stress level, from the heart rate variability.

Figure 7D:
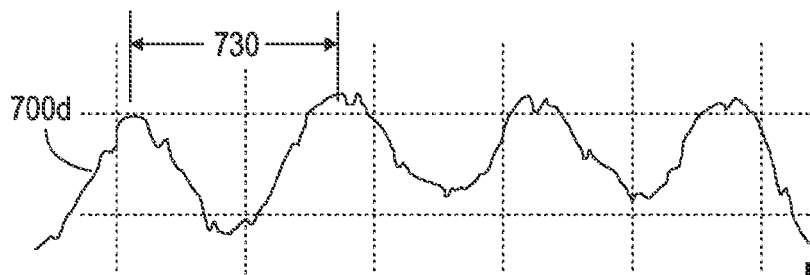

The respiration signal 700d of FIG. 7D is easier to extract than heartbeat signals, because the light loss caused by respiration biomechanical movement is much larger than the light loss caused by heartbeat movements. In some embodiments, the heartbeat signal is not filtered out from the respiration waveform. In sonic embodiments, a respiration rate calculation is performed by the processor 606 by identifying a peak value of each breathing waveform to get a time difference 730 between two respiration cycles.

Methods of Use

Figure 8:
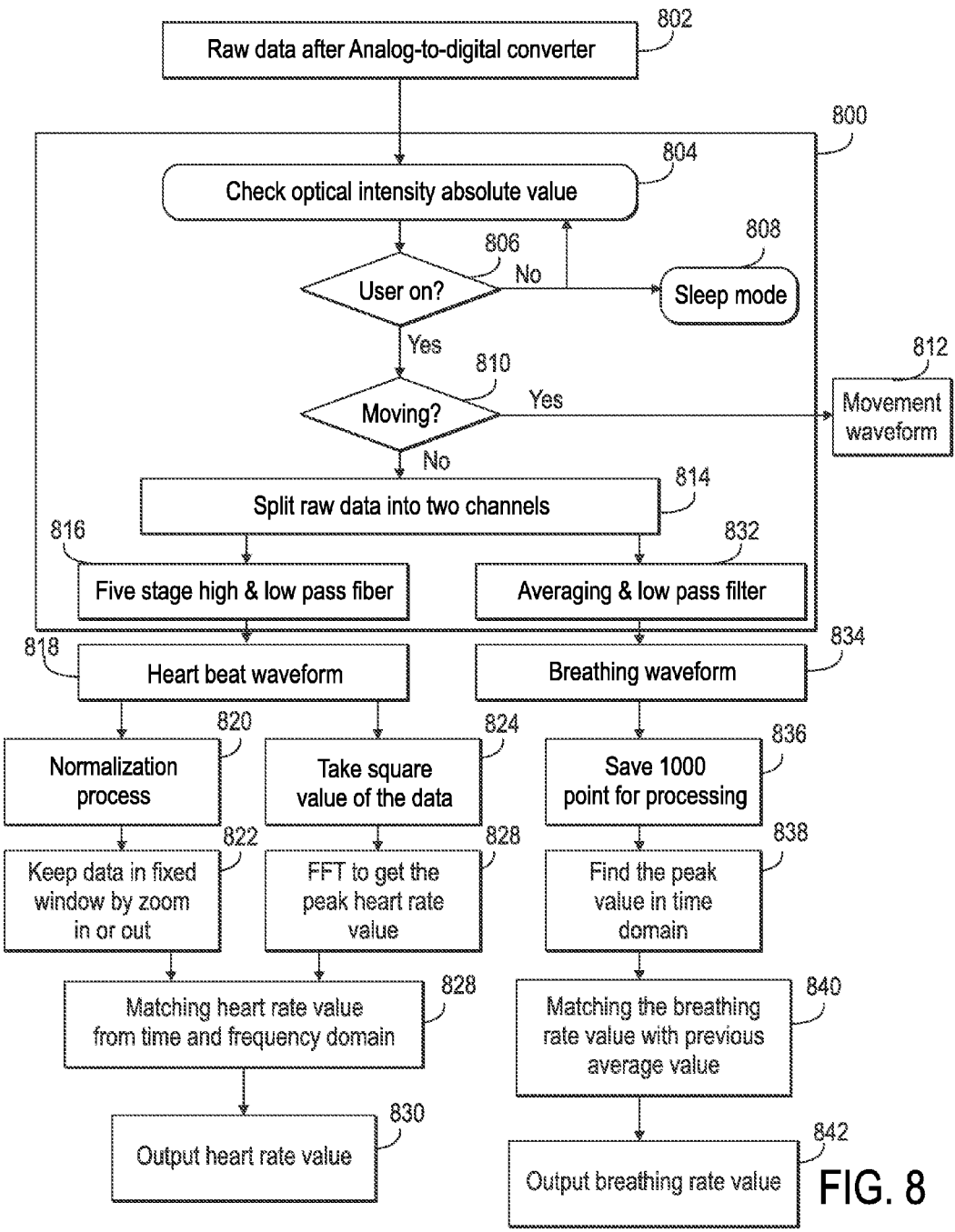
FIG. 8 is a flow chart illustrating of one embodiment of a method for filtering and analyzing data acquired by an intensity-based fiber optic sensor system, in accordance with the teachings of the present disclosure.

FIG. 8 illustrates one embodiment of a signal filtering and data analysis process 800 performed by a processor of the presently described optical fiber sensor monitoring system. Signal processing can be performed to extract the heartbeat/respiration waveforms from the raw signal when a user is on the sensor and not moving a lot. Such a process may be performed, for example, by the processor 606 of FIG. 6. In some embodiments, the processor receives raw digital data from an analog-to-digital converter, as shown at block 802. When a digital signal is received, the optical intensity absolute value may be checked, as shown at block 804. When an optical intensity absolute value is known, the processor of some embodiments compares the received signal to the optical intensity absolute value to determine whether a user is on the sensor, as shown at block 806. If a user is on the sensor, there is significant light loss and a resultant decline in optical intensity. When a user is not on the sensor, the hardware of some embodiments operates in sleep mode to save battery power, as shown at block 808. When high light loss is detected, the processor of some embodiments proceeds to determine whether the user is moving, as shown at block 810. If the processor detects repeated or continual relatively large light loss changes, the processor defines this moment as a moving moment and outputs a movement waveform, as shown at block 812. If the light intensity remains relatively constant with little changes, this moment may be defined as a heartbeat/respiration processing moment and the raw digital data signal is split into two channels, as shown at block 814.

In the illustrated embodiment, at block 816, the signal in one channel undergoes multiple stages of filtering. In one embodiment, five stages of high and low band pass filtering is performed to remove the noise in the raw data and isolate the heartbeat waveform, as shown at block 818. There are many methods that may be used to process the heartbeat waveform. In various embodiments, a method is used that is relatively simple and requires low processing power, so as to be suitable for performance by a portable sensor having relatively low processing and battery capabilities. In some embodiments, a combination of time domain and frequency domain analysis is used to get a robust heartbeat value. In such embodiments, the heartbeat waveform is split into two channels. One channel is for time domain analysis, while another channel is for frequency domain analysis, in time domain analysis, a normalization process 820 is performed to make data consistent for ease of analysis. Data may be kept in one fixed window by zooming in and zooming out, as shown at block 822. In frequency domain, data is squared, as shown at block 824, and a Fast Fourier Transformation is performed at 826 to get the peak frequency. The peak frequency is the heartbeat rate. Heartbeat rate matching is done at block 828 to reduce error rate. In various embodiments, the processor outputs a heartbeat rate value at 830.

In some embodiments, another channel of the raw digital signal is processed at block 832 by averaging the signal and applying a low pass filter. A breathing waveform is output at block 834. In some embodiments, a time window of multiple data points, for example, 1000 data points, is saved at block 836 to find the peak value in the time domain at block 838. By identifying the peak value of the respiration waveform, the respiration rate can be obtained, and average respiration rate may be matched to the latest respiration rate at block 840 to get a breathing rate. As shown at block 842, in some embodiments, the processor outputs the breathing rate.

Figure 9A:
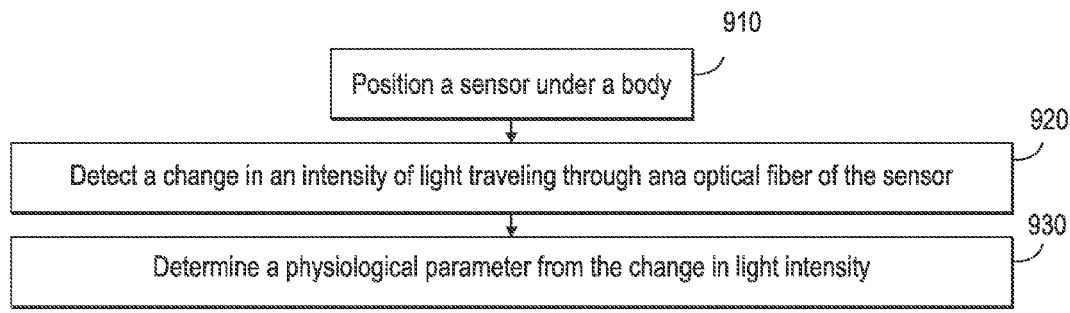
FIGS. 9A and 9B are flow charts illustrating one embodiment of a method of detecting a physiological parameter with an intensity-based fiber optic sensor system, in accordance with the teachings of the present disclosure.
Figure 9B:
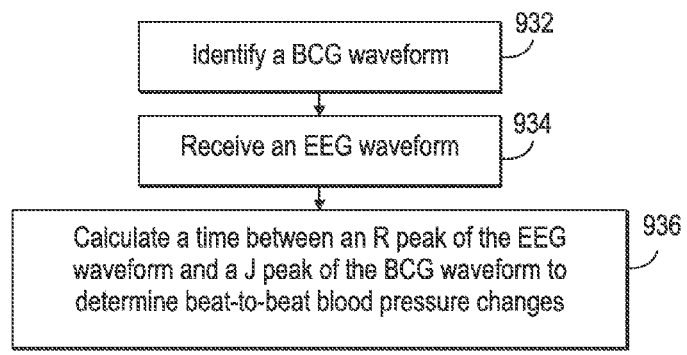

The optical fiber sensors and associated methods of signal filtering and data analysis described above may be used to determine one or more physiological parameters of a patient. One example of a method of determining physiological parameters of a patient is shown in FIGS. 9A and 9B. As shown at block 910, in various embodiments a sensor is positioned under the body of a patient. The patient may be positioned to stand, sit, or lay on the sensor. The sensor may be any optical sensor embodiment described in the present disclosure. At block 920, the system detects a change in an intensity of light traveling, through an optical fiber of the sensor. In various embodiments, the change in light intensity is detected at a light receiver and processed by a processor. As described above, the change in light intensity corresponds to fiber deformation caused by a movement of the body. The movement of the body may be a micro-movement (such as breathing or a heartbeat) or a macro-movement (such as a shift in body position). Using the methods of FIG. 8 or other methods known to those skilled in the art, the processor of the provided optical fiber sensor determines a physiological parameter from the change in light intensity, as shown at block 930. The physiological parameter may be, for example, a BCG waveform, a heart rate, a breathing rate, or other vital sign or parameter of interest.

In some embodiments, determining the physiological parameter includes determining beat-to-beat blood pressure changes. As shown in FIG. 9B, such a determination may be performed by identifying a BCG waveform, as shown at block 932 and described in detail above, receiving an EEG waveform, as shown at block 934, and calculating a time between an R peak of the EEG waveform and a J peak of the BCG waveform, as shown at block 936. The EEG waveform may be received by a processor from an EEG sensor. In some embodiments, the EEG sensor is external to the optical fiber sensor described herein. The time between the R peak and the J peak is indicative of the beat-to-beat pressure change.

In some embodiments, methods performed by a healthcare professional include placing a fiber optic sensor, such as any of the single deformer structure sensors described herein, under a patient. The sensor may be disposed, for example, within a seat cushion, chair, bed, mattress, mattress pad, rug, mat, or any other suitable structure on which a patient can sit, lay, or stand. The method performed by the healthcare professional may further include activating the sensor and viewing physiological parameters output by the sensor. In some embodiments, the physiological parameter includes a BCG waveform. The method of some embodiments further includes diagnosing a health condition, at least in part, from abnormalities detected in the BCG waveform.

Figure 10A:
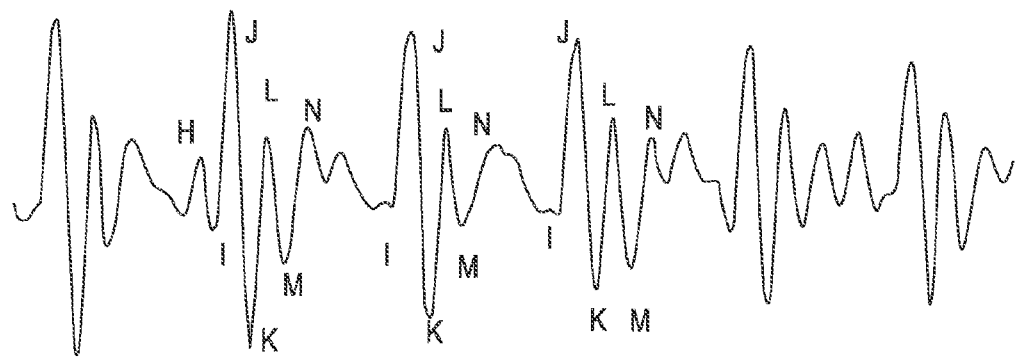
FIGS. 10A and 10B illustrate ballistocardiograph waveforms acquired, respectively, by a prior art optical fiber sensor system and an optical fiber sensor system of the present disclosure.
Figure 10B:
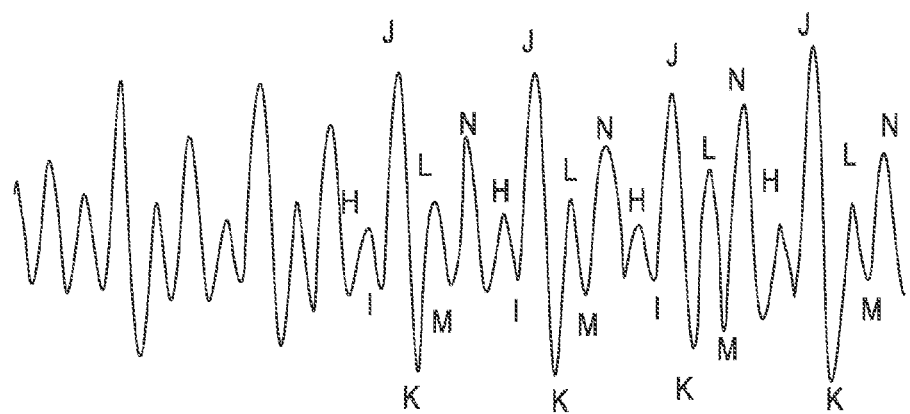

In various embodiments disclosed herein, the optical fiber sensor is configured to acquire very clear, reliable, and reproducible BCG waveforms. While some semblance of a BCG waveform may be detectable by some existing optical fiber sensors having a dual deformer structure, the waveforms are insufficient for clinical monitoring and diagnostic purposes. For example, the BCG waveforms acquired by prior art systems are often unreliable due to noise and inaccuracies that result when the layers of the deformer become misaligned. Moreover the BCG waveforms acquired by prior art systems are unstable. A clear, stable BCG waveform includes several characteristic features including features conventionally denoted as H, I, J, K, L, M, and N. As shown in FIG. 10A, a BCG waveform acquired by one prior art system generated a very unstable BCG waveform in which the H wave is frequently missing. In contrast, one embodiment of the system of the current disclosure produced the very clear, stable, reliable, and reproducible BCG waveform of FIG. 10B.

In some methods of use, such a reliable BCG waveform may be relied on by a healthcare professional to facilitate diagnosis of one or more health conditions. For example, identification of a characteristic abnormality in a BCG waveform may be used to help diagnose angina pectoris, asymptomatic coronary artery disease, acute myocardial infarction, hypertension, coarctation of the aorta, mitral stenosis, and other cardiac conditions, as described, for example, in E. Pinheiro et al., "Theory and Developments in an Unobtrusive Cardiovascular System Representation: Ballistocardiography," *The Open Biomedical Engineering Journal*, 2010, 4, pp. 201-216, the contents of which is herein incorporated by reference in its entirety.

CONCLUSION

As used in the description and claims, the singular form "a", "an" and "the" include both singular and plural references unless the context clearly dictates otherwise. For example, the term "a sensor" may include, and is contemplated to include, a plurality of sensors. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed invention. "Consisting of" shall mean that the devices, systems, and methods include the recited elements and exclude anything more than a trivial or inconsequential element or step. Embodiments defined by each of these transitional terms are within the scope of this disclosure.

While embodiments described herein include the terms "patients," "person," and/or "individual" for simplicity of description, it will be appreciated by one skilled in the art that various embodiments described herein are applicable to, and contemplated to be applied to, monitoring of vital signs in any mammal, including pets, livestock, and healthy individuals such as office workers, babies, or others who are not patients in a healthcare setting.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A sensor for detecting a physiological parameter, the sensor comprising:
 a multi-mode optical fiber comprising an inner core, a cladding layer, and an outer coating, wherein a core diameter is greater than 50% of a cladding diameter;
 an LED (light emitting diode) light source coupled to a first end of the optical fiber;
 an LED driver electrically coupled to the LED light source and configured to regulate a power level of the LED light source;
 a receiver coupled to a second end of the optical fiber, the receiver configured to sense changes in an intensity of light traveling through the optical fiber; and
 a deformer structure is a single mesh layer formed of mesh having openings disposed therein, wherein a surface area of the openings is between 30% and 60% of a total surface area of the mesh layer;
 wherein the optical fiber is arranged in a plane in contact with a surface of the deformer structure such that an application of force onto the sensor results in a first portion of the optical fiber bending into an opening of the mesh layer and a second portion of the optical fiber flexing against the mesh;

a total diameter of the optical fiber consists of a diameter across the inner core, the cladding layer, and the outer coating;

the mesh layer is formed of interwoven fibers;

wherein a diameter of each interwoven fiber is ±25% of the total diameter of the optical fiber.

2. A sensor for detecting a physiological parameter, the sensor comprising:

a multi-mode optical fiber comprising an inner core, a cladding layer, and an outer coating, wherein a core diameter is greater than 50% of a cladding diameter;

an LED (light emitting diode) light source coupled to a first end of the optical fiber;

an LED driver electrically coupled to the LED light source and configured to regulate a power level of the LED light source;

a receiver coupled to a second end of the optical fiber, the receiver configured to sense changes in an intensity of light traveling through the optical fiber; and a deformer structure is a single mesh layer formed of mesh having openings disposed therein, wherein a surface area of the openings is between 30% and 60% of a total surface area of the mesh layer;

wherein the optical fiber is arranged in a plane in contact with a surface of the deformer structure such that an application of force onto the sensor results in a first portion of the optical fiber bending into an opening of the mesh layer and a second portion of the optical fiber flexing against the mesh;

a total diameter of the optical fiber consists of a diameter across the inner core, the cladding layer, and the outer coating;

wherein each opening of the single mesh layer is 100% to 300% of the total diameter of the optical fiber.

* * * * *